United States Patent [19]

Cardenas et al.

[11] 4,292,459

[45] Sep. 29, 1981

[54] COUPLING REACTION INVOLVING A GRIGNARD AND ALLYLIC HALIDE

[75] Inventors: Carlos G. Cardenas; Zia Ud Din, both of Jacksonville, Fla.

[73] Assignee: SCM Corporation, New York, N.Y.

[21] Appl. No.: 786,973

[22] Filed: Apr. 13, 1977

Related U.S. Application Data

[63] Continuation-in-part of Ser. No. 596,273, Jul. 16, 1975, abandoned, Ser. No. 596,426, Jul. 16, 1975, abandoned, Ser. No. 596,274, Jul. 16, 1975, abandoned, and Ser. No. 596,361, Jul. 16, 1975, abandoned.

[51] Int. Cl.$^3$ .............................................. C07C 1/26
[52] U.S. Cl. ...................................... 585/641; 585/469
[58] Field of Search ........... 260/666 A, 677 R, 680 R; 585/641, 469

[56] References Cited

U.S. PATENT DOCUMENTS 3,948,803  4/1976  Carney ............................ 260/666 R

OTHER PUBLICATIONS

Kharasch et al., "Grignard Reactions of Nonmetallic Substances" (1954), Prentice-Hall, New York pp. 1157 to 1165.

Tamura et al., "Journal of Organometallic Chemistry", 42 (1972) pp. 205 to 210.

*Primary Examiner*—Curtis R. Davis
*Attorney, Agent, or Firm*—Richard H. Thomas; Merton H. Douthitt

[57] ABSTRACT

Disclosed is a process for the coupling of a Grignard reagent RMgX with an allylic halide in the presence of a dipolar aprotic solvent wherein the improvement, for obtaining improved yield and selectivity, comprises adding a catalyst to said Grignard or allylic halide and then carrying out the coupling reaction by the addition of the Grignard reagent to the allylic halide, said reaction being characterized by the displacement at the gamma position (relative to the halide) of the allylic halide with R of the Grignard reagent, migration of the allylic double bond in the direction of the halogen atom and loss of halogen. The present invention also resides in the discovery of certain novel procedures for the synthesis of Vitamin E. Specific embodiments of this aspect of the invention reside in the syntheses of 6,7-dehydrophytol, 10,11-dihydrofarnesene, phytone, hexahydropseudoionone, and related compounds as precursors for Vitamin E.

10 Claims, No Drawings

COUPLING REACTION INVOLVING A GRIGNARD AND ALLYLIC HALIDE

The present application is a continuation-in-part of prior application Ser. No. 596,273, filed July 16, 1975; application Ser. No. 596,426, filed July 16, 1975; application Ser. No. 596,274, filed July 16, 1975; and application Ser. No. 596,361, also filed July 16, 1975, all in the name of Carlos G. Cardenas and Zia Ud Din, all of which are now abandoned and all of which are assigned to assignee of the present application.

The present invention relates to the coupling of two compounds together wherein one of the compounds is a Grignard reagent and the other is an allylic halide.

The present invention is particularly applicable to coupling a Grignard with an allylic halide having multiple reactive sites. A typical such allylic halide is a terpene-derived hydrocarbon of the 2,6-dimethyloctane series, such as chloromyrcene (3-chloro-6-methylene-2-methylocta-1,7-diene).

BACKGROUND OF THE INVENTION

The coupling reaction of an alkyl halide and a Grignard reagent has been known for some time and, when catalyzed by a transition metal catalyst (which includes metal complexes and salts), is known as the Kharasch Reaction.[1,2,3] Unfortunately, both yield and selectivity are usually low and the reaction is suitable only for special cases.

[1] *Journal of Organometallic Chemistry*, 42, 205,206 (1972), M. Tamura and J. Kochi.
[2] *Journal of Organometallic Chemistry*, 31, 289 (1971), M. Tamura and J. Kochi.
[3] *Bulletin of the Chemical Society of Japan*, 48, 2389 (1975), Y. Ohbe and T. Matsuda.

An allylic halide has been coupled with a benzylic halide employing the Wurtz reaction, but here again selectivity and yield has been low due to self-coupling (i.e., coupling of two molecules of the allylic halide) along with the desired cross-coupling (of the allylic halide with the benzylic halide). Disproportionation and hydrogen-abstraction have also contributed to lack of selectivity and low yield.

An added problem found in using allylic halides is that the cross-coupling can produce a mixture resulting from both direct displacement and displacement with allylic rearrangement. In the former, the halogen atom is simply displaced by the R group of the Grignard. In the latter, the R group attaches itself to the gamma carbon (with respect to the halide) of the allylic halide group with migration of the double bond in the direction of the halogen atom and loss of halogen.

Recently, advances have been made in the use of these coupling reactions for the synthesis of certain compounds. It is reported in *Bull. Chem. Soc. Japan*, 45, 2947 (1972) by Ohbe and Matsuda, with regard to the reaction of an allylic halide and an alkyl Grignard reagent in the presence of a transition metal salt, that three reactions occur competitively: (a) reduction of the allylic halide to the olefin, (b) cross-coupling of the halide and alkyl Grignard reagent, and (c) self-coupling of the allylic halide. It is indicated that in the case of allyl chloride, the ratio of cross-coupled product to self-coupled product ranges from about 83:17 to about 12:88. The coupling reaction was carried out employing ethereal solutions of the allylic halide and alkyl Grignard reagent.

Two other publications, *Synthesis*, 303 (1971), and *Journal of Organometallic Chemistry*, 42, 205 (1972), both by M. Tamura and J. Kochi, describe the use of tetrahydrofuran (THF) as a solvent for the coupling of Grignard reagents and alkyl halides. The coupling reactions are copper catalyzed, and it is disclosed that the organometallic intermediates are more stable in tetrahydrofuran than in conventional solvents. The publication does not deal with allylic halides, but simply points out that the reaction is mostly applicable to primary bromides and that "secondary and tertiary alkyl halides generally give poor yields of coupled products and disproportionation predominates." Under the Tamura and Kochi conditions, cross-coupling is by far the predominant reaction with the yield of self-coupled dimers being negligibly small.

More recently, Mesnard and Miginiac reported, [*C. R. Acad. Sci., Ser. C.*, 277 (14), 567 (1973),] high selectivity for displacement with allylic rearrangement in the reaction of 1,4-dihalo-2-butenes (a primary allylic halide) and saturated Grignard reagents. The coupling reaction was carried out employing ethereal solutions of both reagents and no catalyst.

Besides employing different solvents in the above works, the authors of the three studies used significantly different experimental procedures. The Ohbe et al. method involved refluxing the ether-Grignard reagent solution with the metal catalyst for approximately one hour followed by rapid addition of the allylic halide to the solution and continued refluxing. The Tamura and Kochi method involved addition of the copper catalyst to a stirred and cooled (less than 0° C.) solution of the alkyl halide and Grignard in tetrahydrofuran. The Mesnard and Miginiac procedure involved addition of the Grignard solution to the allylic dihalide at $-10°$ C. followed by stirring at ambient temperature for 24 hours.

SUMMARY OF THE INVENTION

The present invention resides in the discovery that a Grignard reagent and an allylic halide can be coupled in the presence of a dipolar aprotic solvent, with a high degree of selectivity in favor of displacement with allylic rearrangement, i.e., displacement with R of the Grignard reagent at the gamma position with respect to the halogen atom of the allylic halide, migration of the double bond in the direction of the halogen atom, and loss of halogen, by adding a catalyst to either the Grignard reagent or to the allylic halide and carrying out the reaction in a homogeneous catalytic reaction by the sequence of addition of the Grignard reagent to the allylic halide.

Whereas the present invention encompasses the use of dipolar aprotic solvents broadly, a preferred dipolar aprotic solvent which can be employed in the process of the present invention is tetrahydrofuran (THF). Another preferred dipolar aprotic solvent is hexamethylphosphoramide (HMPA). A mixture of ether with THF (e.g., up to 80% ether and 20% THF) may also be employed.

The catalyst, which can be characterized as a Kharasch Reaction catalyst, may be added either to the Grignard or to the allylic halide, but must be added prior to addition of the Grignard to the halide and must have at least limited solubility in the substrate/solvent solution to which it is added. Preferred catalysts offering a high degree of selectivity are cuprous and cupric salts such as cuprous chloride, cupric chloride, and lithium tetrachlorocuprate ($Li_2CuCl_4$). A ferric salt such as ferric chloride is another catalyst offering a high degree of selectivity.

For purposes of the present application, a Kharasch reaction catalyst is defined as a catalyst by which cross-coupling and allylic rearrangement substantially predominate under the conditions of reaction used, to the substantial exclusion of self-coupling of moles of allylic halide and direct displacement of the halide by the R group of the Grignard reagent.

The present invention has been successfully practiced with a number of allylic halides, and the present invention is not limited to a particular allylic halide or class of halides. The invention, however, finds particular application with secondary allylic halides wherein the halide is a halogen derivative of an unsaturated terpene hydrocarbon of the 2,6-dimethyloctane series, such as beta-myrcene (3-methylene-7-methylocta-1,6-diene). Beta-myrcene is reacted with $Cl_2$ to give chloromyrcene (3-chloro-6-methylene-2-methylocta-1,7-diene).

Other unsaturated terpene hydrocarbons which can be halogenated and then coupled with a Grignard are alpha-myrcene (6-methylene-2-methylocta-1,7-diene); beta-ocimene (3,7-dimethylocta-1,3,6-triene); alpha-ocimene (3,7-dimethylocta-1,3,7-triene); and citronellene (3,7-dimethylocta-1,6-diene).

The present invention also is applicable to certain substituted allylic halides, for instance wherein the allylic halide is derived from a ketone, such as alpha-methylheptenone (2-methylhept-1-en-6-one). The chloro derivative of this compound is 2-chloromethyl-hept-1-en-6-one, which is a primary allylic halide. Another suitable ketone is beta-methylheptenone (2-methylhept-2-en-6-one), the chloro derivative of which is 3-chloro-2-methylhept-1-en-6-one.

The present invention is not applicable to allylic halides which have a reactive group which could consume the Grignard reagent. It is noteworthy, however, that neither ketones (alpha-methylheptenone) nor esters interfere even though these are functional groups that would be expected to interfere. Acidic functional groups do interfere as would be expected by one skilled in the art.

In the broad sense of the present invention, the R of the Grignard reagent RMgX (X being a halogen) can be any saturated (alkyl) or mono- or di-unsaturated (alkenyl) compound, or a vinyl, aryl, aralkyl or alicyclic compound. The present invention is particularly applicable, however, to aliphatic Grignard reagents. Typical reactants for forming the Grignard reagent for coupling with the above allylic halides are ethyl chloride, 3-methylbutylchloride, 3,7-dimethyloctyl chloride, 3-methyl-1-butene, and 3,7-dimethyl-1,6-octadiene. These compounds are converted readily to the respective Grignards, e.g., ethyl magnesium chloride, 3-methylbutyl magnesium chloride, 3,7-dimethyloctyl magnesium chloride, 3,7-dimethyloct-6-enyl magnesium chloride, and 3-methylbut-2-enyl magnesium halide. (Bromides and iodides are also operable.)

By the present invention, a high degree of selectivity in the coupling reaction both as to cross-coupling (vs. self-coupling) and displacement with allylic rearrangement (vs. direct displacement) can be achieved. The addition of the Grignard reagent to the allylic halide preferably is carried out slowly.

The temperature at which the coupling reaction is carried out and proportions are not critical. As a general rule, the coupling reaction proceeds with more selectivity at lower temperatures, for instance below about 0° C. The reaction is exothermic and preferably should be run at less than room temperature for optimum yield and selectivity. With regard to proportions, it is desirable to substantially consume the allylic halide in the coupling reaction to reduce interference in subsequent purification, but this is a matter of convenience.

Preferred halogens in the process of the present invention are chlorine, bromine and iodine.

The present invention also resides in the discovery of certain novel procedures for the synthesis of Vitamin E, and precursors therefor. In one aspect, the invention resides in the discovery of a novel route to Vitamin E via the synthesis of the $C_{20}$ molecule dehydrophytol (3,7,11,15-tetramethylhexadeca-2,6-dien-1-ol) by first preparing the Grignard 3,7-dimethyloctyl magnesium chloride, then coupling that with chloromyrcene to produce a $C_{20}$ triene, and converting the triene to dehydrophytol. In the broadest sense of the present invention, the coupling can be carried out by any of the procedures of the prior art, for instance that of Tamura and Kochi [*Synthesis*, 303 (1971)], but preferably the coupling is carried out by procedures D or E of Example 1 (vide infra) in the presence of a dipolar aprotic solvent and a Kharasch Reaction catalyst in the sequence of adding the catalyst to either the Grignard reagent or to the allylic halide and carrying out the reaction in a homogeneous catalytic reaction by the sequence of addition of the Grignard reagent to the allylic halide. The synthesis of Vitamin E is then carried out by coupling dehydrophytol with trimethylhydroquinone in a condensation reaction to produce 3,4-dehydro-Vitamin E, which is readily reduced to Vitamin E. Unsaturated $C_{10}$ Grignard compounds, preferably alkenyl or alkadienyl compounds, having the same arrangement of carbon atoms as 3,7-dimethyloctyl magnesium chloride, such as 3,7-dimethyloct-6-enyl magnesium chloride, can also be used to synthesize other polydehydro-phytol compounds and Vitamin E. By the term polydehydrophytol, it is meant compounds having the same arrangement of carbon atoms as dehydrophytol but different or additional points of unsaturation.

Other $C_{10}$ hydrocarbon acyclic derivatives than chloromyrcene, of the 2,6-dimethyloctane series, having the potential for forming an allylic halide such as α-myrcene (6-methylene-2-methylocta-1,7-diene), β-ocimene (3,7-dimethylocta-1,3,6-triene), and α-ocimene (3,7-dimethylocta-1,3,7-triene) also can be used in the process of the present invention.

In another novel aspect of the present invention, Vitamin E is prepared by coupling chloromyrcene with 3-methylbutyl magnesium chloride to produce 10,11-dihydrofarnesene (3-methylene-7,11-dimethyldodeca-1,6-diene). This compound is then converted to phytone (2,6,10-trimethylpentadecan-14-one), which is a known precursor for isophytol (3,7,11,15-tetramethylhexadec-1-en-3-ol). Isophytol is readily coupled with trimethylhydroquinone following known procedures to produce Vitamin E. The conversion is carried out by hydrohalogenating 10,11-dihydrofarnesene to produce 1-chloro-3,7,11-trimethyldodeca-2,6-diene and then reacting that with sodiomethylacetoacetate followed by saponification and decarboxylation. This product (6,10,14-trimethylpentadeca-5,9-dien-2-one) is then hydrogenated to phytone.

Here also, the invention in its broadest sense, relating to the synthesis of 10,11-dihydrofarnesene, can be carried out by any of the procedures of the prior art, for instance that of Tamura and Kochi (vide supra), but preferably is carried out by the procedure D or E of Example 1 (vide infra). Also, the invention is applicable broadly to the preparation of farnesene itself (3-methylene-7,11-dimethyldodeca-1,6,10-triene), for instance by employing as a starting material the Grignard 3-methylbut-2-enyl magnesium chloride; or isomers of farnesene; or isomers of 10,11-dihydrofarnesene; or compounds having the same arrangement of carbon atoms as 10,11-dihydrofarnesene but one or two fewer points of unsaturation. Also, this aspect of the invention is applicable employing as the allylic halide $C_{10}$ hydrocarbon acyclic terpene derivatives of the 2,6-dimethyloctane series other than chloromyrcene.

A third aspect of the present invention resides in an alternative synthesis of long chain, aliphatic ketones such as phytone (2,6,10-trimethylpentadecan-14-one) and hexahydropseudoionone (2,6-dimethylundecan-10-one), both valuable intermediates or precursors for Vitamin E. This aspect of the invention resides principally in the discovery that certain aliphatic $C_8$ ketones such as methylheptenone (2-methylhept-1-en-6-one or 2-methylhept-2-en-6-one) can be halogenated to produce halides allylic to a terminal olefin, and then can be coupled with a monohalide $C_{10}$ or $C_5$ aliphatic Grignard compound, described above with regard to the syntheses of dehydrophytol and dihydrofarnesene, to produce phytone and hexahydropseudoionone, respectively.

In a preferred form of the invention, the carbonyl group of the $C_8$ ketones, either before or subsequent to halogenation, is "blocked" or protected by the formation of an ethylene ketal. This may, for instance, be accomplished by reacting the $C_8$ ketone with ethylene glycol to produce an ethylene ketal.

As above, this aspect of the present invention, in its broadest sense, can be carried out by any of the procedures of the prior art (for instance, the prior art of Example 1, vide infra), but preferably the invention is carried out by procedures D or E of the present invention.

The principles of the present invention are illustrated in the following Examples. In Example 1, comparative data is given on the coupling reaction of ethyl magnesium bromide and chloromyrcene (3-chloro-6-methylene-2-methylocta-1,7-diene) illustrating the advantages of the present invention over the methods of Ohbe et al., Tamura and Kochi, and Mesnard and Miginiac described above.

In the following Examples all yields given are theory yields, while all other percentages given are percentages by weight and temperatures are in degrees Centigrade.

EXAMPLE 1

In this Example, comparative data was obtained on the coupling of ethyl magnesium bromide with chloromyrcene in accordance with the following equation:

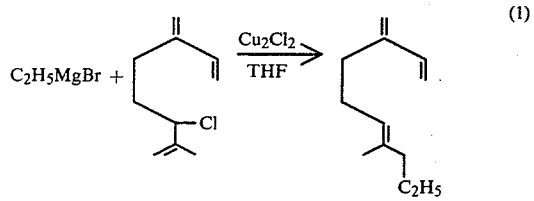
(1)

Chloromyrcene (3-chloro-6-methylene-2-methylocta-1,7-diene) is a terpenic allylic chloride which can be prepared by a number of ways, for instance by the methods described in prior U.S. Pat. Nos. 2,995,600 (Webb) and 3,031,442 (Webb), incorporated by reference herein.

It is stated in U.S. Pat. No. 2,995,600 that the method is applicable to the preparation of novel chlorides of the unsaturated 2,6-dimethyloctane series from acyclic 10 carbon atom terpenes containing a terminal dimethyl group adjacent to a double bond as represented by the following structural formula:

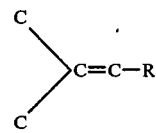

R being the remainder of the terpene molecule. By contacting one mole of chlorine with the desired olefin, the chlorination occurs at the double bond, which is thereby shifted and a hydrogen ion is expelled to form an allylic chloride. The reaction is a substitution reaction resulting in the formation of hydrogen chloride. Preferably, with the more reactive hydrocarbons such as beta-myrcene and beta-ocimene, the chlorination is carried out in the presence of a hydrogen chloride acceptor such as sodium carbonate or sodium bicarbonate.

The formation of allylic chlorides is also applicable to acyclic terpenes having an isopropenyl terminal group, such as alpha-myrcene and alpha-ocimene, following the teachings of U.S. Pat. No. 3,031,442.

The Grignard ethyl magnesium bromide was prepared by standard methods. Equimolar amounts of the Grignard reagent and chloromyrcene were employed.

Several procedures were used in the coupling reaction. In those employing a catalyst, the reaction was carried out using cuprous chloride ($Cu_2Cl_2$) as the catalyst. These procedures are indicated in the second column of the following Table 1, the procedures being as follows:

Procedure A—This procedure corresponds to the Ohbe et al. method in which the Grignard solution was stirred with a catalyst at about 35° for one hour. The allylic chloride was then added quickly at the desired reaction temperature and stirring was continued for three additional hours.

Procedure B—This procedure corresponds to the Tamura and Kochi method, except that Tamura and Kochi were not concerned with a reaction wherein one of the reactants was an allylic halide. The Grignard reagent and allylic chloride were first stirred together at the desired reaction temperature, and then the catalyst was added.

Procedure C—This procedure corresponds to the Mesnard and Miginiac method in which no catalyst is used and the Grignard solution is added to the allylic chloride at −10° followed by stirring at ambient temperature for 24 hours.

Procedure D—This procedure is illustrative of the concepts of the present invention. The Grignard solution was stirred with the catalyst at about 35° for one hour, and then was added to the allylic chloride over a one-hour period and stirred for an additional hour, at the desired reaction temperature.

Procedure E—This procedure represents a modification of Procedure D and is also illustrative of the concepts of the present invention, the distinction being that the Grignard solution was added slowly to a stirred mixture of the allylic chloride and catalyst at the desired reaction temperature.

In analyzing the reaction product, the formation of $C_2$ and $C_4$ compounds derived from the ethyl moiety was ignored, and instead, the ratio of cross-coupled ($C_{12}$) to self-coupled ($C_{20}$) compounds, and the ratio of products derived by displacement with allylic rearrangement relative to products derived by direct displacement were determined. These data are given in the sixth and seventh columns, respectively, of the following Table 1. The eighth column of the Table is the yield of $C_{12}$ cross-coupled compound in the product, based on theoretical yield, estimated by inspection of gas chromotographic data. The ninth column gives the percentage of chloromyrcene which was converted or reacted.

The remaining columns of Table 1 give the solvents that were employed with the coupling reactants (the third and fourth columns), and the temperature of the reaction mixture (the fifth column). Again, the catalyst employed in all instances was cuprous chloride ($Cu_2Cl_2$), whenever a catalyst was employed.

In the Table, the designation "EtMgBr" means ethyl magnesium bromide. The designation "Cl Myr" means chloromyrcene.

However, Runs 5 and 6 still suffer from substantial direct displacement (29 and 23 percent, respectively) and relatively low $C_{12}$ percent yield.

Run 7, using the Mesnard and Miginiac procedure, gave an improved yield of $C_{12}$ but still gave only 77% selectivity for displacement with allylic rearrangement. When Run 7 was repeated in THF solvent (Run 8), the results were similar with slightly lower yield and selectivities.

Runs 9 and 10 of the present invention were carried out at 35° and −7°, respectively, and it is evident that temperature has little effect. Run 10, however, using a lower temperature and placing the catalyst with the chloromyrcene, shows somewhat improved conversion. Notably, both runs show very high (97%) selectivity for displacement with allylic rearrangement and also very high yield of $C_{12}$ (94%) and selectivity for cross-coupling (99% and 100%).

Runs 11 and 13 were carried out using the procedures of Runs 9 and 10, but employing ether as the diluting solvent. These runs resulted in either low cross-coupling or low yield. Run 12 was carried out with the procedure of Run 6 (analogous to the Tamura and Kochi procedure) and a relatively low yield was obtained.

To summarize, the discovery of the present inven-

TABLE 1

| Run | Procedure | Solvent EtMgBr | Solvent Cl Myr | Temp | $C_{12}/C_{20}$ | $C_{12}$ Allylic Rearrang. Direct Displ. | $C_{12}$ Yield % | Cl Myr Conv. |
|---|---|---|---|---|---|---|---|---|
| 1 | A | Ether | None | 35° | 0/100 | — | 0 | 80% |
| 2 | A | Ether | Ether | 35° | 16/84 | — | <1 | 21 |
| 3 | A | THF | None | 35° | 39/61 | 73/27 | 28 | 72 |
| 4 | A | THF | THF | 35° | 57/43 | 72/28 | 35 | 65 |
| 5 | A | THF | THF | −7° | 100/0 | 71/29 | 60 | 58 |
| 6 | B | THF | THF | −7° | 100/0 | 77/23 | 86 | 61 |
| 7 | C | Ether | Ether | −10°→25° | 98/2 | 77/23 | 89 | 49 |
| 8 | C | THF | THF | −10°→25° | 93/7 | 73/27 | 86 | 44 |
| 9 | D | THF | THF | 35° | 99/1 | 97/3 | 94 | 60 |
| 10 | E | THF | THF | −7° | 100/0 | 97/3 | 94 | 74 |
| 11 | D | Ether | Ether | 35° | 16/84 | 78/22 | <1 | 28 |
| 12 | B | Ether | Ether | −7° | 100/0 | 92/8 | 29 | 42 |
| 13 | E | Ether | Ether | −7° | 99/1 | 91/9 | 52 | 58 |

The only runs within the scope of the present invention are Runs 9 and 10. These show almost no self-coupling in that nearly one hundred percent of the product was $C_{12}$ compound as compared to $C_{20}$ compound (the sixth column). The seventh column shows that there was little direct displacement, about 97% of the product being the result of displacement with allylic rearrangement. Column 8 shows that there was a substantial $C_{12}$ percent yield (about 94%).

Still referring to the Table, Run 1 verifies that self-coupling predominates using the Ohbe et al. method. Run 2 shows that further dilution (of the chloromyrcene with ether) does not have a major effect on the course of the reaction, but simply decreases conversion. Substitution of THF for ether (Run 3) shows a dramatic increase in the amount of cross-coupling, which is further increased by dilution (Run 4). The selectivity for cross-coupling (column 6) becomes 100 percent in Run 5 when the effect of THF and dilution is combined with a decrease in temperature to −7°. Run 6 shows that the allylic halide, chloromyrcene, reacts readily using the Tamura and Kochi procedure, even though it is a secondary halide. The fact that it is allylic is certain to increase its reactivity and the predominance of cross-coupling is analogous to that reported by Tamura and Kochi.

tion, as evidenced by the above data, resides in the discovery that the addition of the Grignard solution to the allylic halide, employing dilution with an aprotic solvent such as THF and further employing a transition metal catalyst, results in a strong selectivity for displacement with allylic rearrangement in the cross-coupling reaction, and also improved yield of the cross-coupling product.

EXAMPLE 2

The effect of the catalyst on the selectivity towards displacement with allylic rearrangement was studied using 3,7-dimethyloctyl Grignard and chloromyrcene and the results are shown in the following Table 2. It is evident from this Table that catalysts containing cuprous and cupric ions are preferred. Improved results were also obtained with a ferric ion containing catalyst. The desired product of reaction is 3-methylene-7,11,15-trimethylhexadeca-1,6-diene.

The preparation of dimethyloctyl Grignard is as follows. Initially, myrcene hydrochloride (1-chloro-3,7-dimethylocta-2,6-diene) may be prepared from myrcene by reaction with hydrogen chloride or by other means, all described in the aforementioned U.S. Pat. No. 3,031,442. For instance, referring to Example 1 of such patent, the myrcene hydrochloride is prepared by adding one mole of anhydrous hydrogen chloride to one mole of myrcene (95+% by ultraviolet spectroanalysis) in the presence of 0.5% of cuprous chloride at 10°–20° C. The reaction product contains 75–80% geranyl plus neryl chloride (myrcene hydrochloride), 5–10% linalyl chloride, 10–15% terpinyl chloride plus traces of other chlorides and hydrocarbons.

The dimethyloctyl chloride is then obtained by reacting the myrcene hydrochloride (neryl/geranyl chloride) with sodium acetate and saponifying the acetate with sodium hydroxide to produce nerol/geraniol. This is then hydrogenated to produce dimethyloctanol, which is treated with HCl in the presence of zinc chloride to produce the dimethyloctyl chloride.

Preferably, the Grignard of dimethyloctyl chloride is prepared by first placing 14.4 grams (0.6 moles) of magnesium turnings under nitrogen in 150 ml. of a co-solvent solution of tetrahydrofuran and ether having a mole ratio of 3:1, respectively. Dimethyloctyl chloride is dissolved separately in an additional 150 ml. of the co-solvent solution, in an amount of 88.2 grams (0.5 mole). A few ml. of the dimethyloctyl chloride solution are added to the magnesium containing solution with a crystal of iodine, and the mixture is heated to reflux, followed by the addition of 2–3 ml. of ethyl bromide. Once the reaction is started, the remaining dimethyloctyl chloride is added rapidly while under reflux, and the reaction mixture is stirred and refluxed over a period of about 2½ hours. The resulting 3,7-dimethyloctyl magnesium chloride is then decanted into a suitable receiving vessel.

In the following Table, the fifth and sixth columns give results obtained in terms of ratio of allylic rearrangement to direct displacement and ratio of cross-coupling to self-coupling. The latter was computed on the basis of products obtained by direct displacement as well as products obtained by allylic rearrangement. Most of the runs were carried out using the Procedure E in which the Grignard solution was added slowly to a stirred mixture of the allylic chloride and the catalyst.

Specifically, chloromyrcene (77 grams of 90% purity or about 0.4 moles) was dissolved in 200 ml. of tetrahydrofuran and 0.7 grams of cuprous chloride ($Cu_2Cl_2$) was then added, and the reaction mixture was cooled to about $-7°$ C. The solution containing the Grignard compound was then added very slowly over a period of about 4.5 to 5 hours while the temperature was maintained at less than about $-7°$ C. After the addition, the reaction mixture was allowed to come to room temperature slowly over about 1.5 hours. It was again cooled to about 0° and slowly quenched with dilute, cold hydrochloric acid ($\sim 0.5$ N) until a clear solution was obtained. The aqueous portion was extracted with pentane and the combined oils were washed with water and with saturated NaCl solution. Analysis was by vapor-phase chromotography.

It is preferable to add the Grignard slowly to the chloro-olefin so that at no stage is there excess Grignard which by a relatively slower displacement reaction could form the self-coupled dimer by-product.

Run 17 employed Procedure B (using essentially the same proportions) in which the Grignard solution was stirred with the allylic chloride and then the catalyst was added (following the teachings of Tamura and Kochi). This run confirmed the results of Example 1, namely that inadequate displacement by allylic rearrangement results, although the run demonstrates that substantial cross-coupling is achieved rather than self-coupling. Run 18 employed a slightly different procedure (labeled Procedure F) in which the Grignard solution and the catalyst were stirred briefly at room temperature and then this solution was added slowly to the allylic chloride. This is closely analogous to the Procedure D disclosed above and within the concepts of the present invention.

It will be apparent from the Table that the Runs 14, 15, 16, 18, 19, 25 and 26 are within the scope of the present invention. These runs employed either cupric, cuprous, or ferric ion catalysts. From column 5, it is evident that the displacement was substantially by allylic rearrangement.

From column 6, it is evident that little self-coupling was experienced, particularly in those runs within the scope of the present invention. The self-coupling which did occur was of the Grignard to form 2,6,11,15-tetramethylhexadecane (as distinguished from self-coupling of the allylic halide experienced when following the teachings of Ohbe et al.).

In Runs 20, 21 and 23, using nickel and cobalt catalysts, no coupling was observed under the conditions of time and temperature employed. However, some degree of conversion to $C_{10}$ hydrocarbons was noted. In Run 22, also using a nickel chloride catalyst, but a higher reaction temperature, insufficient conversion was observed. The same is true of Run 24 with cobalt chloride catalyst, and a higher temperature.

TABLE 2

| | | THE EFFECT OF CATALYST ON THE SELECTIVITY | | | |
|---|---|---|---|---|---|
| Run | Procedure | Catalyst | Temp. °C. | Allylic Rear./ Dir. Disp. | Crosscoupling/ Selfcoupling |
| 14 | E | $Cu_2Cl_2$ | $-7$ | 99/1 | 98/2 |
| 15 | E | $Li_2CuCl_4$ | $-7$ | 97/3 | 97/3 |
| 16 | E | $CuCl_2$ | $-7$ | 95/1 | 94/6 |
| 17 | B | $Li_2CuCl_4$ | $-7$ | 56/44 | 94/6 |
| 18 | F | $Li_2CuCl_4$ | $-7$ | 98/2 | 96/4 |
| 19 | E | $FeCl_3$ | $-7$ | 93/7 | 92/8 |
| 20 | E | $Ni(AcAc)_2$ | $-7$ | NR | NR |
| 21 | E | $NiCl_2$ | $-7$ | NR | NR |
| 22 | E | $NiCl_2$ | 25 | 70/30 | 85/15 |
| 23 | E | $CoCl_2$ | $-7$ | NR | NR |
| 24 | E | $CoCl_2$ | 25 | 65/35 | 85/15 |
| 25 | E | $Cu_2Cl_2$ | $+20$ | 92/8 | 94/6 |
| 26 | E | $Cu_2Cl_2$ | $-20$ | 99/1 | 98/2 |

The principal advantage of the present invention lies in the fact that compounds that are new or were heretofore available only with difficulty can now be synthesized with great simplicity and selectivity. The following Examples are illustrative.

EXAMPLE 3

This Example illustrates the preparation of dehydrophytol and Vitamin E, from 3-methylene-7,11,15-trimethylhexadeca-1,6-diene prepared by the procedure of Example 2 (Procedure E). The synthesis can be represented by the following equations:

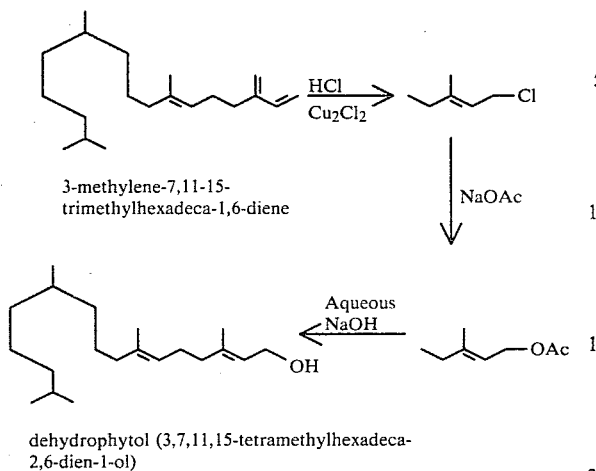

3-methylene-7,11-15-trimethylhexadeca-1,6-diene dehydrophytol (3,7,11,15-tetramethylhexadeca-2,6-dien-1-ol)

Initially the starting triene is hydrochlorinated using the procedure of a prior U.S. Pat. No. 3,016,408 (Robert L. Webb) with Cu₂Cl₂ plus HCl. The resulting chloride is then reacted with sodium acetate containing tetrabutylammonium chloride. Alternatively, the procedure of a prior U.S. Pat. No. 3,066,847 (Donald A. Fortune) with ammonium acetate or of U.S. Pat. No. 3,076,839 (Robert L. Webb) with Cu₂Cl₂, ammonium acetate and acetic acid may be employed. The crude acetate following washing is then saponified with aqueous sodium hydroxide solution containing Aliquat 336 catalyst (a quaternary ammonium compound, trademark General Mills) at 95°–105° C. to produce crude 6,7-dehydrophytol. The procedure of this latter step and refining of the 6,7-dehydrophytol also follow the disclosure of aforementioned prior U.S. Pat. No. 3,031,442 (Webb). The disclosures of all the aforementioned patents are incorporated herein by reference.

In a specific example, 86.2 grams (0.312 mole) of the triene was added to a suitable vessel along with 0.8 gram of cuprous chloride (Cu₂Cl₂), and the mixture was stirred and cooled to about −3°. Dry hydrogen chloride was then passed slowly into the mixture so that all of the gas was consumed and none escaped. The reaction was conducted slowly, over a few hours' period with the addition of 11.7 grams (0.32 mole) of the hydrogen chloride. The mixture was then further stirred for 2 hours at about −3° and kept cold overnight, to produce 98.7 grams of the hydrochloride.

Sodium acetate powder (68.4 grams) was then added to the above hydrochloride (98.7 grams) plus 21.9 grams of sodium carbonate, and 170 mls. of 1:1 DMF/benzene and 2.6 grams of tetrabutylammonium chloride. The mixture was mechanically stirred and heated to 102°–105° and kept at that temperature for 4 hours under nitrogen. The product was cooled and worked up with pentane, yielding 107.2 grams of the acetate.

The acetate of the above step (100 grams), 317 grams of 50% sodium hydroxide, and 0.3 gram of Aliquat 336 catalyst were then heated to reflux under nitrogen. The temperature of the mixture was about 115°, and the mixture was refluxed for about 2.0 hours and cooled under nitrogen. Eighty-six (86) grams of 6,7-dehydrophytol were obtained giving a theoretical yield of about 74.6% based on triene consumed. It is understood that the term dehydrophytol includes dehydroisophytol[4] which is present in the product in the ratio of about 1:10 based on the amount of its isomer in the product. These two compounds give the same product when condensed with TMHQ.

[4] 3,7,11,15-tetramethylhexadeca-1,6-diene-3-ol

If desired, the second step reacting the hydrochloride with sodium acetate can be carried out in the presence of an amount of benzene to reduce viscosity of the reaction mixture. Also, the second step of the above sequence, reacting the acetate with sodium hydroxide, can be carried out with substantially less sodium hydroxide; for instance, about 50 grams. It is also understood that the sequence of 6,7-dehydrophytol can employ the preparation of esters other than the acetate. Thus the present invention is applicable to the preparation of any compound having the group —OOCR wherein R is alkyl, aryl, aralkyl, alkenyl or cycloalkyl. Also, instead of an ester, an ether can be employed, the compound having a $C_{1-4}$ alkoxide group instead of an —OOCR group.

Reaction of 6,7-Dehydrophytol with TMHQ to Produce 3,4-dehydro-Vitamin E

The reaction of isophytol or phytol with TMHQ is well known. One method that has been employed with phytol is described in Japan Kokai No. 73 48,472 [Chem. Abstr. 79, 105067m (1973)]. It was discovered that a similar method could also be applied successfully in condensation of TMHQ with dehydrophytol. Essentially, 2.5 grams TMHQ and 0.1 gram aluminum powder were placed in a flask to which was added 35 mls. of ethyl acetate containing 1 ml. of boron trifluoride etherate. While stirring, 4 grams of dehydrophytol was added slowly and the mixture was refluxed for 4 hours at 80°. This gave 5.0 grams of crude dehydrotocopherol (dehydro-Vitamin E) after work-up and removal of unreacted starting materials. A portion of the dehydrotocopherol obtained (1.0 gram) was conveniently hydrogenated in 30 mls. glacial acetic acid containing 0.5 gram of 5% Pd on BaSO₄. Shaking for 8 hours under 52 psig H₂ pressure and ambient temperature provided 1.0 gram of crude α-tocopherol (Vitamin E). The present invention has been described with reference to the use of beta-myrcene to produce chloromyrcene (3-chloro-6-methylene-2-methylocta-1,7-diene) which is then coupled with 3,7-dimethyloctyl magnesium chloride. The invention is equally applicable to the use of alpha-myrcene, or alpha- or beta-ocimene.

Alpha-myrcene (6-methylene-2-methylocta-1,7-diene) is chlorinated to 2-chloromethyl-6-methyleneocta-1,7-diene. This is reacted with dimethyloctyl magnesium chloride to produce 3,7-dimethylene-11,15-dimethylhexadec-1-ene. This compound yields 7-methylene-3,11,15-trimethylhexadec-2-en-1-ol which, when reacted with TMHQ and hydrogenated, produces Vitamin E.

The sequence with beta-ocimene is equally as analogous. In this sequence, beta-ocimene (3,7-dimethylocta-1,3,6-triene) is chlorinated to yield the monochloride which is then coupled with 3,7-dimethyloctyl magnesium chloride to yield 3,7,11,15-tetramethylhexadeca-1,3,6-triene. This in turn is reacted employing previously discussed procedures to dehydrophytol.

The sequence for alpha-ocimene would be analogous to the above sequence illustrated for alpha-myrcene.

Further alternatives within the scope of the present invention are possible. For instance, it is possible to have condensation of trimethylhydroquinone with precursors of dehydrophytol, for instance with the triene, the hydrochloride or the ester (e.g., acetate). The advantage in condensation of trimethylhydroquinone with dehydrophytol or the ester (acetate) precursor, is that purification of the dehydrophytol or ester is more readily accomplished than purification of the chloride or coupling product, 3-methylene-7,11,15-trimethylhexadeca-1,6-diene.

EXAMPLE 4

Instead of using a saturated, halide-terminated aliphatic compound such as dimethyloctyl chloride (Example 2) to form the Grignard, it is possible to form the Grignard of an unsaturated compound such as citronellyl chloride and to couple that with chloromyrcene resulting in a $C_{20}$ tetraene (3-methylene-7,11,15-trimethylhexadeca-1,6,14-triene). This is then condensed with TMHQ directly or by way of one of the derivatives (e.g., 6,7,14,15-didehydrophytol) of the tetraene is described above. Hydrogenation produces the desired Vitamin E.

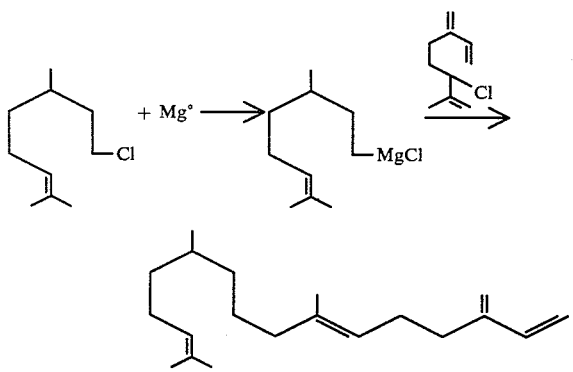

A mixture consisting of 2.5 g (0.104 mole) magnesium, 18.4 g (0.1 mole) of 95% citronellyl chloride, 100 mls. of tetrahydrofuran and one drop of dibromoethane was refluxed for 2 hours to give citronellyl magnesium chloride in almost quantitative yield.

In a 500-ml., three-neck flask equipped with a mechanical stirrer, thermometer and an addition funnel were placed 18.3 g (0.1 mole) of 95% chloromyrcene, 100 mls. of tetrahydrofuran, and 0.1 g of cuprous chloride. The mixture was stirred and cooled to $-7°$. Then the above prepared Grignard was added dropwise during a 2-hour period and the reaction temperature was maintained at $-7°$ during the addition. Upon completion of addition, the reaction mixture was quenched with diluted hydrochloric acid (2%) at 0° and worked up using pentane solvent. The combined organic portion was filtered through magnesium sulfate and the solvent evaporated in a rotary evaporator to give 32.5 g of product containing 46% of the $C_{20}$ tetraene, thus a 54.6% theory yield. The selectivity for displacement with allylic rearrangement was 96.3%.

EXAMPLE 5

This Example illustrates an alternative method for preparation of the alkenyl Grignard, of Example 4, from an olefin. The Grignard is then coupled with chloromyrcene to give the same $C_{20}$ tetraene.

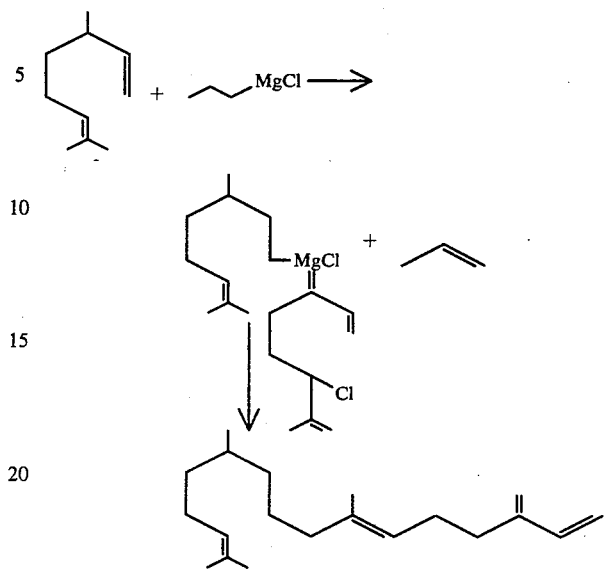

In a one-liter, three-neck flask equipped with an addition funnel, thermometer, stirrer and condenser were placed 7.2 g (0.3 mole) of magnesium, 300 mls. of ether and 23.6 g (0.3 mole) of n-propyl chloride. The reaction mixture was stirred gently and refluxed for 3 hours. At the end of that period almost all the magnesium had reacted to give n-propyl magnesium chloride.

The reaction mixture was stirred vigorously and cooled at 0°. Then 38.3 g (0.25 mole) of 90% 3,7-dimethyl-1,6-octadiene was added at 0° during 10 minutes. Dicyclopentadienyltitanium dichloride (3.5 g) was then added in one portion at $-2°$ and an exothermic reaction was observed. The reaction mixture was allowed to come to room temperature slowly and then refluxed. After 18 hours, 77% of the 3,7-dimethyl-1,6-octadiene had been converted to citronellyl magnesium chloride.

Ether (200 mls.) was distilled at 35°–50° from the reaction mixture while 300 mls. of THF was added slowly from the addition funnel.

In a 500-ml., three-neck flask equipped with a mechanical stirrer, thermometer and an addition funnel were placed 18.5 g (0.1 mole) of 93% chloromyrcene, 100 mls. of tetrahydrofuran and 0.1 g of cuprous chloride. The mixture was stirred and cooled at $-7°$ and 150 mls. (0.096 mole) of the above-prepared citronellyl magnesium chloride solution was added over a 2-hour period. Upon completion of addition the reaction mixture was quenched with diluted hydrochloric acid ($\sim 2\%$). The usual work-up gave 35.5 g of a product containing 37.95% of the $C_{20}$ tetraene, thus a 41.6% theory yield. The selectivity for displacement with allylic rearrangement was 18 99%.

EXAMPLE 6

This Example illustrates the preparation of 10,11-dihydrofarnesene (3-methylene-7,11-dimethyldodeca-1,6-diene) useful in the synthesis of phytone (2,6,10-trimethylpentadecan-14-one) and Vitamin E. The synthesis can be represented by the following equations:

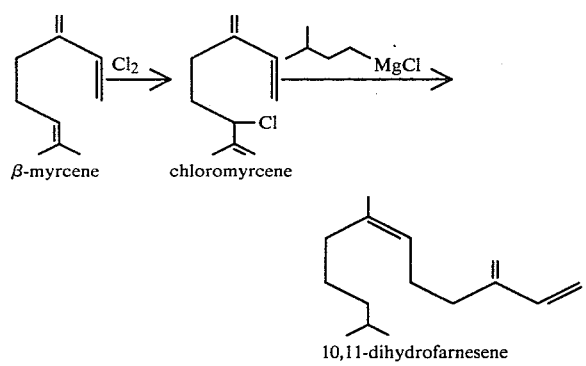

β-myrcene  chloromyrcene 10,11-dihydrofarnesene

One of the starting compounds, 3-methylbutyl magnesium chloride, was prepared employing the following ingredients:

| | |
|---|---|
| magnesium turnings | 13.4 grams (0.551 mole) |
| 1:1 solution of ether and tetrahydrofuran (THF) | 200 mls. |
| 3-methylbutyl chloride (98.8% purity) | 53.9 grams (0.50 mole) |

The magnesium turnings were placed in a 250-milliliter, 3-neck, round-bottom flask equipped with a condenser, mechanical stirrer and two addition funnels. After drying the system by heating under nitrogen, 50 mls. of the ether/THF solution were added along with a crystal of iodine. About 5 milliliters of the 3-methybutyl chloride was added and the mixture was brought to reflux by gentle heating. Addition of 5 drops of ethyl bromide caused the reaction to initiate at which time the iodine color disappeared. The remainder of the 3-methylbutyl chloride was added dropwise over a 40-minute period while 150 milliliters of the ether/THF solution was added via the second addition funnel. A gentle reflux was maintained throughout and was continued for 1.5 hours after completion of addition. On cooling and settling, the Grignard solution was filtered and the volume was adjusted to 600 milliliters by the addition of THF. A total of 1.1 grams (0.045 mole) of magnesium was recovered.

Examples were given above for the preparation of chloromyrcene from beta-myrcene. In this Example, chloromyrcene was prepared by placing sodium carbonate (200 grams) in a flask with 505.2 grams of beta-pinene pyrolysate which analyzed at 80.9% beta-myrcene (408.7 grams, 3.00 moles). The reactor was flushed with nitrogen and then, while stirring in the dark at 25°±2° C. chlorine (160.4 grams, 2.3 moles) was added via a fritted glass tube over a 220-minute period. Stirring was continued for thirty minutes after completion of addition at which time the solids were removed by filtration providing 584.7 grams of crude chloromyrcene. Gas chromotographic analysis without an internal standard indicated 70.3% conversion of beta-myrcene and 89.7% theory yield of 3-chloro-6-methylene-2-methylocta-1,7-diene (chloromyrcene).

Dihydrofarnesene was then prepared employing the following starting materials:

| | |
|---|---|
| crude chloromyrcene | 111.2 grams (~0.4 mole) |
| tetrahydrofuran (THF) | 380 mls. |
| cuprous chloride | 0.3 gram |
| 3-methylbutylmagnesium chloride solution | 600 mls. |

The crude chloromyrcene (111.2 grams), tetrahydrofuran (380 mls.) and powdered cuprous chloride (0.3 gram) were stirred under nitrogen in a 2-liter, 3-neck, round-bottom flask and cooled to −7°. The Grignard solution (600 mls.) was then added over a 125-minute period while maintaining the reaction temperature at about −7°. On completion of addition, the cooling bath was removed and the reaction mixture was stirred for two hours as it came to room temperature. Quenching of the reaction was effected by the addition of 500 mls. of 0.5 N HCl at 0°–5°, after which the oil and water layers were separated. The aqueous layer was extracted twice with 100 ml. portions of pentane and the combined oils were washed once with 1 liter of $H_2O$ and with 500 mls. saturated aqueous NaCl. The oils were filtered through magnesium sulfate and stripped of solvent on a rotary evaporator. Stripping at 10 mm and at 1 mm provided 109 grams of material which analyzed as 12.1% beta-myrcene (13.15 grams, 0.097 mole) and 59.6% 10,11-dihydrofarnesene (64.92 grams, 0.318 mole). This corresponded to an 83% conversion of beta-myrcene in the beta-pinene pyrolysate and a 67% theory yield of 10,11-dihydrofarnesene (b.p. 70° at 0.3 mm pressure) based on beta-myrcene consumed. Conversion of chloromyrcene was quantitative.

The reaction steps to phytone (2,6,10-trimethylpentadecan-14-one) involve first forming the ketone, 6,10,14-trimethylpentadeca-5,9-dien-2-one, and then hydrogenating the ketone under conventional hydrogenation conditions to phytone. Forming the ketone (6,10,14-trimethylpentadeca-5,9-dien-2-one) requires first hydrohalogenating 10,11-dihydrofarnesene to produce 1-chloro, 3,7,11-trimethyldodeca-2,6-diene, and then reacting that compound with sodiomethyl acetoacetate followed by saponification and decarboxylation. The reaction sequence is analogous to the known conversion of myrcene to geranyl acetone and then further to hexahydropseudoionone, and employs essentially the same reaction conditions.

The concepts of the present invention are applicable to the preparation of 10,11-dihydrofarnesene and its isomers from $C_{10}H_{16}$ acyclic terpene hydrocarbons other than beta-myrcene such as alpha-myrcene (6-methylene-2-methylocta-1,7-diene), alpha-ocimene (3,7-dimethylocta-1,3,7-triene), and beta-ocimene (3,7-dimethylocta-1,3,6-triene). For instance in the case of alpha-myrcene, the compound 3,7-dimethylene-11-methyldodec-1-ene is obtained. This isomer is readily converted, with or without purification, to phytone following the principles set forth above with respect to the conversion of 10,11-dihydrofarnesene from beta-myrcene. The compound beta-ocimene, following halogenation, is readily coupled with 3-methylbutylmagnesium chloride to produce 3,7,11-trimethyldodeca-1,3,6-triene, an isomer of 10,11-dihydrofarnesene. Similarly, alpha-ocimene is readily coupled, following halogenation, with 3-methylbutylmagnesium chloride to produce 7-methylene-3,11-dimethyldodeca-1,3-diene. As with the products of reaction employing alpha-myrcene, these isomers are readily converted to phytone employing the principles set forth above.

The temperature at which the coupling reaction is carried out and proportions are not critical. As a general rule, the coupling reaction proceeds better at lower temperatures, for instance below about 0° C. The reaction is exothermic and preferably should be run at less than room temperature for optimum yield and selectivity. With regard to proportions, it is desirable to substantially consume the allylic halide in the coupling reaction to reduce interference in subsequent purification, but this is a matter of convenience.

EXAMPLE 7

This Example illustrates the preparation of phytone from 10,11-dihydrofarnesene.

Crude 10,11-dihydrofarnesene (59.9% pure, 122.6 g, 0.356 mole) prepared as in Example 6, was placed in a 250-ml., 3-neck, round-bottom flask with 0.5 g $Cu_2Cl_2$ powder and stirred magnetically at −5° C. Dry hydrogen chloride (14.0 g, 0.384 mole) was then added via a fritted glass tube over a 30-minute period and then stirring was continued for an additional 30 minutes. The yield of crude chloride was 135.2 g, with gas chromotographic analysis indicating complete consumption of 10,11-dihydrofarnesene.

Sodiomethylacetoacetate was prepared by adding an excess of methylacetoacetate (74.3 g, 0.64 mole) to a solution of sodium ethoxide (31.3 g, 0.46 mole) in 150 mls. absolute ethanol at 25°. The reaction mixture was cooled to 0° and then the crude chloride prepared above was added dropwise over a 25-minute period and stirring was continued at 0° for an additional 3 hours. After this period, the temperature was allowed to rise to ambient over a 40-minute period. A portion of the ethanol (78.0 g) was distilled at this point by stirring the reaction mixture at 60°–65° for 2 hours under a slight vacuum. After cooling to 30°, 550 mls. of 10% aqueous NaOH was added over a 15-minute period and the reaction mixture was stirred at 70° for 4 hours. After settling, the layers were separated and the aqueous layer was saturated with NaCl and extracted with three 200-ml. portions of pentane. The combined oils were washed once with 1 liter $H_2O$ and once with 1 liter saturated NaCl to yield, after solvent removal, 139.2 g of crude 6,10,14-trimethylpentadeca-5,9-dien-2-one. Gas chromotographic analysis indicated 53.2% purity which represents an estimated theory yield from 10,11-dihydrofarnesene of 78.8%.

A portion of this material (124.8 g) was dissolved in 500 mls. methanol and hydrogenated in the presence of 2.0 g of 5% Pd on carbon at 80–100 psig for 24 hours. Fractionation gave pure phytone b.p. 122°–124° (0.6 mm) identical to an authentic sample.

EXAMPLE 8

This Example represents the synthesis of phytone from the alpha-isomer of methylheptenone (2-methyl-hept-1-en-6-one). Th synthesis involves first reacting methylheptenone with ethylene glycol to form the ketal [2-methyl-2-(4-methylpent-4-en-1-yl)-1,3-dioxolane] of alpha-methylheptenone. This is followed by chlorination to produce as a major product, the ethylene ketal of 2-chloromethylhept-1-en-6-one, which is then coupled with 3,7-dimethyloctylmagnesium chloride to produce 2-methyl-2-(4-methylene-8,12-dimethyltridec-1-yl)-1,3-dioxolane. This compound is subjected to hydrogenation and aqueous acid treatment, in either order, to produce phytone (2,6,10-trimethylpentadecan-14-one).

Reaction of methylheptenone and ethylene glycol

The preparation of the ketal of methylheptenone follows conventional procedures for addition of an alcohol to a ketone. The following reactants were employed.

| Compound | Weight |
| --- | --- |
| alpha-methylheptenone | 500 grams |
| benzene | 500 mls. |
| ethylene glycol | 50 grams |
| oxalic acid | 2.0 grams |

These reactants were added in the order listed to a vessel and were stirred under nitrogen and then warmed to reflux temperature of 80° C. The reflux was carried out for 6 hours trapping 8.7 mls. of water in a Dean-Stark Trap. Benzene was then distilled off to a pot temperature of 110° C. giving 430 mls. of benzene. The reaction mixture was cooled to room temperature, and 100 grams of sodium acetate was added and stirred for 10 minutes. An additional 20 mls. of water was added and stirred for 5 minutes.

The reaction mixture was allowed to stand overnight, and an organic layer weighing 86.1 grams was separated and stripped of solvent, yielding 63.2 grams of product which was determined to be 83.5% alpha-methylheptenone ketal [2-methyl-2-(4-methylpent-4-en-1-yl)-1,3-dioxolane] and 3.6% alpha-methylheptenone. This provided as follows:

| | |
| --- | --- |
| Percent Conversion | 95.4% |
| Weight Yield | 110.6% |
| Yield as a Percentage of Theoretical | 82.0% |

The catalyst found to be most useful in this reaction was oxalic acid. However, many catalysts of intermediate strength such as oxalic acid can be employed, and the present invention is not limited to a particular catalyst.

Chlorination of Alpha-methylheptenone Ketal

A starting reaction mixture containing the following ingredients was prepared:

| | |
| --- | --- |
| alpha-methylheptenone ketal (83.8%) | 6.1 grams (0.03 mole) |
| dimethylformamide | 50 mls. |
| sodium carbonate | 10 grams |

The ingredients were stirred under nitrogen in the dark at about 25° C. Subsequently, chlorine was added over about a 3.5-minute period, in the amount of 2.3 grams. Solids were removed from the reaction product by filtration. The product was then mixed with 100 mls. saturated sodium bicarbonate ($NaHCO_3$) solution, and pentane extraction and stripping resulted in an oil yield of 6.3 grams. Gas chromatographic analysis showed 25.2% alpha-methylheptenone ketal and 17.5% of the desired 2-methyl-2-(4-chloromethylpent-4-en-1-yl)-1,3-dioxolane for a conversion as follows:

| | |
| --- | --- |
| Percent Conversion | 69.0% |
| Weight Yield | 31.3% |
| Yield as a Percentage | |

| | |
|---|---|
| of Theoretical | 26.0% |

Coupling of the Ketal with Dimethyloctyl Magnesium Chloride

The ketal from above (0.8 gram or 0.004 mole) in 5 mls. of a solvent mixture (of ether and tetrahydrofuran) was stirred with 0.05 gram of $Cu_2Cl_2$ and cooled to $-5°$ C., and dimethyloctyl Grignard (0.005 mole) prepared by the procedure of Example 2 was added dropwise slowly over a period of 30 minutes. The mixture was allowed to come to room temperature (in about 30 minutes) and was quenched with an acid solution of 5 mls. concentrated hydrochloric acid in 100 mls. water. A product yield of 1.5 grams, or about 36% of theoretical, was obtained. The major product was identified as 2-methyl-2-(4-methylene-8,12-dimethyltridec-1-yl)-1,3-dioxolane. Infrared analysis showed that the ketal structure of this compound was intact.

Preparation of Phytone

The conversion of the above product to phytone is straightforward. The reaction is carried out very simply by hydrogenation in methanol using 50 psig hydrogen and Raney nickel catalyst at room temperature. Hydrolysis was effected by stirring at room temperature with 6.4 parts of 10% aqueous HCl for 26 hours.

EXAMPLE 9

This Example illustrates the synthesis of phytone wherein the alpha-ketone (2-methylhept-1-en-6-one) is chlorinated directly to 2-chloromethylhept-1-en-6-one which is then coupled with 3,7-dimethyloctyl magnesium chloride and hydrogenated, as in Example 8.

Specifically, the following ingredients were added to a vessel, in the dark, under nitrogen at about 25° C.:

| | |
|---|---|
| 2-methylhept-1-en-6-one | 64.1 grams (0.5 mole) |
| dimethylformamide | 300 mls. |
| sodium carbonate ($Na_2CO_3$ powdered) | 106 grams (1.0 mole) |

Chlorine (36.5 grams) was added over a 30-minute period at about 25°±2° C. On completion of addition, the mixture was stirred for about 15 minutes at about 25° C., and solids were filtered out. The organic layer was washed with 500 mls. of water, and the mixture was allowed to settle for 2 hours. An organic bottom layer was then recovered weighing about 57.2 grams. Gas chromatographic analysis showed 23.2% alpha-methylheptenone and 15.5% of the desired 2-chloromethylhept-1-en-6-one. These figures correspond to 78.6% conversion and 14.2% theory yield of the monochloride.

The above product (monochloro-methylheptenone) was readily coupled with 3,7-dimethyloctyl magnesium chloride. This was accomplished as follows:

The Grignard of 3,7-dimethyloctyl chloride was prepared by mixing 0.9 gram of 3,7-dimethyloctyl chloride with 0.15 gram of magnesium in 10 mls. of solvent (3 mls. of ether plus 7 mls. of THF). An iodine crystal and a drop of ethyl bromide were added to initiate the reaction.

The chloroketone from above (0.7 gram or 0.004 mole) in 5 mls. of the solvent mixture was stirred and cooled to $-5°$ C. in the presence of a trace of $Cu_2Cl_2$.

The above prepared Grignard (0.005 mole) was then added slowly dropwise at about $-5°$ C. over a 30-minute period. The reaction mixture was stirred at $-5°$ C. for about 30 minutes and then quenched by the dropwise addition of about 5 mls. of 0.5 N hydrochloric acid. After addition of about 10 mls. of $H_2O$, extraction with pentane followed by stripping provided 1.5 grams of oil. Hydrogenation provided phytone, as shown by vapor phase chromatography and mass spectral analysis, at a yield of about 38% based on theoretical.

EXAMPLE 10

This Example is similar to Example 8 except that the ketal is formed after chlorination and prior to coupling with the Grignard.

Alpha-methylheptenone was chlorinated following the procedure of Example 9. The chlorine product (2-chloromethylhept-1-en-6-one) was then reacted with ethylene glycol to form the ketal, 2-methyl-2-(4-chloromethylpent-4-en-1-yl)-1,3-dioxolane, using the following reactants:

| | |
|---|---|
| chloride from Example 9 | 1.0 gram |
| benzene | 50 mls. |
| ethylene glycol | 2.5 grams |
| oxalic acid | 0.1 gram |

The above components were added to a vessel, in the order listed, and were stirred under nitrogen at a reflux temperature of about 80° C. Water which was given off was trapped, and the refluxing was carried out for about 5 hours until no more water was obtained, giving 0.2 ml. of water. Benzene was distilled off to a pot temperature of 110° C. (44 mls.). The above mixture was then cooled to room temperature, and 0.5 gram of sodium acetate was added and stirred for 10 minutes. An additional 5 mls. of water was added and stirred for 5 minutes. The mixture was allowed to settle, and an organic layer, 3.4 grams, was obtained. This was stripped and dried giving an oil yield of 1.0 gram. Gas chromatographic analysis indicated a quantitative yield of the chloride of alpha-methylheptanone ketal [2-methyl-2-(4-chloromethylpent-4-en-1-yl)-1,3-dioxolane]. This product can then be coupled with 3,7-dimethyloctyl magnesium chloride following the procedure of Example 8 to yield, in successive steps, phytone.

EXAMPLE 11

This Example illustrates the concepts of the present invention with the use of beta-methylheptenone (2-methylhept-2-en-6-one).

In essence, beta-methylheptenone is reacted with ethylene glycol following the procedure of Example 8 to yield beta-methylheptenone ketal. This is then reacted with chlorine, also following the procedure of Example 8, to produce 2-methyl-2-(3-chloro-4-methylpent-4-en-1-yl)-1,3-dioxolane.

As an alternative, the beta-methylheptenone can first be chlorinated and then reacted with ethylene glycol to form the ketal.

The allylic chloro ketal was converted to phytone as follows:

The chloro ketal derived from beta-methylheptenone (2.0 grams) was stirred at $-7°$ C. with 30 mls. of THF and 0.05 gram $Cu_2Cl_2$; and 0.025 mole of 3,7-dimethyloctyl magnesium chloride in a THF/ether solution (7/1) was added over a 1-hour period. After completion of addition it was allowed to come to room temperature while continuing to stir. After two hours the reaction mixture was quenched with 0.5 N HCl and worked up in the usual manner. Removal of solvent provided 3.0 grams of crude 2-methyl-2-(4,8,12-trimethyltridec-3-en-1-yl)-1,3-dioxolane which was hydrogenated in methanol using 50 psig hydrogen and 0.3 gram of palladium on carbon catalyst at room temperature. Hydrolysis was effected by stirring at room temperature with 8.3 parts of 10% aqueous HCl for 26 hours. Thus phytone identical by comparison with an authentic sample was produced.

EXAMPLE 12

In this Example, the monochloride derivative of beta-methylheptenone is coupled with 3-methylbutyl chloride ($C_8$ plus $C_5$) and hydrogenated to produce hexahydropseudoionone, an intermediate for the synthesis of Vitamin E.

Beta-methylheptenone (2-methylhept-2-en-6-one) is first reacted with ethylene glycol to produce the ketal (beta-methylheptanone ketal as in Example 11), and then is chlorinated, also as in Example 11, to produce the monochloride of beta-methylheptenone ketal [2-methyl-2-(3-chloro-4-methylpent-4-en-1-yl)-1,3-dioxolane]. This is then coupled with 3-methylbutyl chloride after forming the Grignard of 3-methylbutyl chloride. The resulting ketal is then hydrogenated and subjected to an acidic medium to produce hexahydropseudoionone.

As an alternative, it is possible to form the monochloride first and then the ketal prior to coupling with 3-methylbutyl magnesium chloride or to perform the coupling reaction on the chloro derivative of beta-methylheptenone itself. Also, a mixture of alpha- and beta-methylheptenone or the corresponding ketals can be used.

EXAMPLE 13

This Example describes the preparation of 3-methylbut-2-enyl magnesium halide (an allylic Grignard reagent) and the coupling of it with chloromyrcene to give farnesene, a $C_{15}$ tetraene.

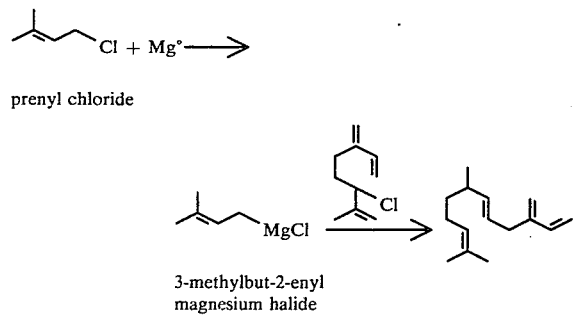

prenyl chloride 3-methylbut-2-enyl magnesium halide

Dry magnesium turnings (6.0 g, 0.25 mole) were placed in a pre-dried 100 ml., three-neck, round-bottom blask equipped with a mechanical stirrer, addition funnel and nitrogen source. While passing nitrogen, the flask and magnesium were re-dried by heating with a hot-air gun. After cooling, 20 mls. of dry THF were added to the flask and stirring was commenced. Prenyl chloride (5.3 g, 0.05 mole) and 20 mls. THF were placed in a syringe pump and added to the magnesium and THF over a period of one hour. Stirring was continued for 1 hour after completion of addition at which point unreacted magnesium was removed by filtration. Separately, a flask containing 10.2 g (0.04 mole) of 67.2% chloromyrcene along with 100 mls. of dry THF and 0.3 g of cuprous chloride were stirred at $-20°$. The prenyl magnesium chloride formed previously was added dropwise over a period of 1 hour while maintaining the temperature at $-20°$. Stirring was continued for 1 hour after completion of addition while allowing the reactants to come to room temperature. After quenching with 50 mls. of 0.05 N HCl, the oils were extracted with pentane and washed with water, with sodium bicarbonate and again with water. Solvent removal provided 14.5 g of product containing farnesene as identified by matching of GC retention times and mass spectral cracking patterns with those of an authentic sample.

It was mentioned or shown that suitable catalysts for use in the process of the present invention are cuprous chloride, cupric chloride, lithium tetrachlorocuprate, ferric chloride, nickel chloride and cobalt chloride. Among Kharasch Reaction catalysts listed in the prior art are the following: ferric chloride; cobalt bromide; nickel chloride; palladium chloride; manganese chloride; cupric chloride; cuprous chloride; silver bromide; ferrous chloride; silver nitrate; $Fe[O_2CC(CH_3)_3]_3$; $Fe(CH_3COCHCOCH_3)_3$; $Fe(CF_3COCHCOCF_3)_3$; $Fe(CH_3COCHCOCH_3)Cl_2$; $Fe(CH_3COCHCOCH_3)_2Cl$; $Fe[(CH_3)_3CCOCHCOC(CH_3)_3]_3$; $Fe(PhCOCHCOPh)_3$;[5] "Ni phosphine complexes"; "Co phosphine complexes"; (aminoalkylferrocenyl)phosphine, e.g., (S)-α-[(R)-2-diphenylphosphinoferrocenyl] ethyldimethylamine, (S)-1-dimethylaminomethyl-2-diphenylphosphinoferrocene, and (R)-1-diphenylphosphine-2-ethylferrocene; nickel-[(−)-2,3-O-isopropylydene-2,3-dihydroxy-1,4-bis(diphenylphosphino)butane]; and copper(I)-N,N,N′,N′-tetramethylethylenediamine.

[5] Ph means phenyl.

It was mentioned with regard to the synthesis of certain aliphatic ketones such as phytone, from $C_8$ ketones such as alpha- or beta-methylheptenone, that a preferred form of the invention resided in protecting the carbonyl group of the $C_8$ ketone by an ethylene ketal. Protection can be accomplished with other groups known to those skilled in the art.

What is claimed is:

1. In the process for coupling a Grignard reagent RMgX, R being alkyl, alkenyl, vinyl, aryl, aralkyl, alicyclic, or alkadienyl, with a secondary allylic halide in the presence of a solvent to form an olefinic hydrocarbon, the improvement for obtaining improved yield and selectivity comprising
   (a) adding a Kharasch reaction catalyst to said Grignard reagent or allylic halide, said solvent being a dipolar aprotic solvent, and then
   (b) carrying out the coupling reaction by the addition of the Grignard reagent to the allylic halide, said reaction being characterized by cross-coupling and allylic rearrangement defined as displacement by the R group of the Grignard reagent at the gamma position relative to the halide of the allylic halide, migration of the double bond in the direction of the halide, and loss of halogen.

2. The process of claim 1 wherein said catalyst is a salt selected from the group consisting of cuprous chloride, cupric chloride, ferric chloride and lithium tetrachlorocuprate.

3. The process of claim 1 wherein said solvent is tetrahydrofuran, hexamethylphosphoramide, or a mixture of tetrahydrofuran and ether.

4. The process of claim 1 wherein said allylic halide is chloromyrcene.

5. The process of claim 1 wherein said allylic halide is a secondary allylic halide and the halogen of the allylic halide is chlorine or bromine.

6. The process of claim 4 wherein said Grignard is 3,7-dimethyloctyl magnesium chloride or 3,7-dimethyloct-6-enyl magnesium chloride.

7. The process of claim 4 wherein said Grignard reagent is 3-methylbutyl magnesium chloride or 3-methylbut-2-enyl magnesium chloride.

8. The process of claim 1 wherein said allylic halide is a secondary allylic halide, and wherein R of aid Grignard reagent is alkyl or alkenyl.

9. The process of claim 8 wherein said secondary allylic halide is an acyclic terpene derivative and said Grignard reagent is a terpene or hemiterpene derivative.

10. A process for the synthesis of an olefinic hydrocarbon from the coupling of a Grignard reagent RMgX, R being an aliphatic group, and a secondary allylic halide, the latter having a terminal olefinic site and a halogen atom allylic to such site, such coupling occurring with displacement by the aliphatic group of the Grignard reagent at the gamma position relative to the halide of the allylic halide, migration of the double bond in the direction of the halide, and loss of halogen, comprising the steps of preparing a reaction mixture comprising said Grinard reagent and said allylic halide by the addition of the Grignard reagent to said allylic halide, said reaction mixture including a Kharasch reaction catalyst and a dipolar aprotic solvent wherein the catalyst was added to either the Grignard reagent or to the allylic halide prior to addition of the Grignard reagent to said allylic halide; and removing from said reaction mixture the olefinic hydrocarbon.

* * * * *